(12) United States Patent
Sperl et al.

(10) Patent No.: US 7,871,401 B2
(45) Date of Patent: Jan. 18, 2011

(54) ABSORBENT ARTICLE WITH IMPROVED FIT

(75) Inventors: Michael Donald Sperl, Waupaca, WI (US); Richard Joseph Kamps, Wrightstown, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1035 days.

(21) Appl. No.: 11/119,195

(22) Filed: Apr. 29, 2005

(65) Prior Publication Data

US 2006/0247593 A1 Nov. 2, 2006

(51) Int. Cl.
*A61F 13/20* (2006.01)

(52) U.S. Cl. .................................. 604/385.27; 604/367

(58) Field of Classification Search ............ 604/385.01, 604/385.03, 367–378
See application file for complete search history.

(56) References Cited

U.S. PATENT DOCUMENTS

| | | | |
|---|---|---|---|
| 2,931,361 A | 4/1960 | Sostrin | |
| 4,036,233 A | 7/1977 | Kozak | |
| 4,100,324 A | 7/1978 | Anderson et al. | |
| 4,443,513 A | 4/1984 | Meitner et al. | |
| 4,560,372 A | 12/1985 | Pieniak | |
| 4,631,062 A | 12/1986 | Lassen et al. | |
| 4,704,116 A | 11/1987 | Enloe | |
| 4,892,536 A | 1/1990 | DesMarais et al. | |
| 4,965,122 A | 10/1990 | Morman | |
| 4,981,747 A | 1/1991 | Morman | |
| 5,114,781 A | 5/1992 | Morman | |
| 5,244,482 A | 9/1993 | Hassenboehler, Jr. et al. | |
| 5,284,703 A | 2/1994 | Everhart et al. | |
| 5,342,341 A * | 8/1994 | Igaue et al. ............ | 604/385.29 |
| 5,350,624 A | 9/1994 | Georger et al. | |
| 5,356,405 A | 10/1994 | Thompson et al. | |
| 5,397,316 A | 3/1995 | LaVon et al. | |
| 5,486,166 A | 1/1996 | Bishop et al. | |
| 5,490,846 A | 2/1996 | Ellis et al. | |

(Continued)

FOREIGN PATENT DOCUMENTS

EP 0 835 088 B1 2/2000

(Continued)

OTHER PUBLICATIONS

International Search Report for PCT/US2006/002078 dated Sep. 22, 2006, 6 pages.

*Primary Examiner*—Michele Kidwell
(74) *Attorney, Agent, or Firm*—Armstrong Teasdale, LLP

(57) ABSTRACT

A stretchable absorbent article has a longitudinal axis, a lateral axis, a front waist region, a back waist region, a crotch region extending longitudinally between and interconnecting said front and back waist regions, a length, and a width. The absorbent article has a liquid impermeable outer cover stretchable in at least one direction and a liner in opposed relationship with the outer cover and stretchable in at least one direction. At least one of the liner and the outer cover has a width substantially equal to the width of the absorbent article along the length thereof. An absorbent structure is disposed between the liner and the outer cover and extends from the crotch region to at least one of the front waist region and the back waist region of the article. The outer cover is elastic and is configured to improve the fit of the absorbent article.

19 Claims, 9 Drawing Sheets

U.S. PATENT DOCUMENTS

| | | |
|---|---|---|
| 5,611,790 A | 3/1997 | Osborn, III et al. |
| 5,624,422 A * | 4/1997 | Allen .................... 604/385.23 |
| 5,645,542 A | 7/1997 | Anjur et al. |
| 5,658,269 A | 8/1997 | Osborn, III et al. |
| 5,804,021 A | 9/1998 | Abuto et al. |
| 5,820,973 A | 10/1998 | Dodge, II et al. |
| 5,846,231 A * | 12/1998 | Fujioka et al. ............... 604/380 |
| 5,873,868 A | 2/1999 | Nakahata |
| 5,964,743 A | 10/1999 | Abuto et al. |
| 6,049,915 A | 4/2000 | Malowaniec |
| 6,231,557 B1 | 5/2001 | Krautkramer et al. |
| 6,262,331 B1 | 7/2001 | Nakahata et al. |
| 6,362,389 B1 | 3/2002 | McDowall et al. |
| 6,413,247 B1 | 7/2002 | Carlucci et al. |
| 6,552,245 B1 | 4/2003 | Roessler et al. |
| 6,641,134 B1 | 11/2003 | Dobbertin et al. |
| 6,645,190 B1 | 11/2003 | Olson et al. |
| 6,682,512 B2 | 1/2004 | Uitenbroek et al. |
| 2002/0022426 A1* | 2/2002 | Curro et al. .................. 442/373 |
| 2003/0023213 A1 | 1/2003 | Fernfors et al. |
| 2003/0097105 A1* | 5/2003 | Chen et al. ................... 604/378 |
| 2004/0122405 A1* | 6/2004 | Van Gompel et al. .. 604/385.22 |

FOREIGN PATENT DOCUMENTS

| | | |
|---|---|---|
| EP | 0591647 A | 10/2006 |
| GB | 2242348 A | 10/1991 |
| GB | 2 305 610 A | 4/1997 |
| WO | WO 93/06805 | 4/1993 |
| WO | WO 00/37009 | 6/2000 |
| WO | WO 03/051254 | 6/2003 |

* cited by examiner

ABSORBENT ARTICLE WITH IMPROVED FIT

FIELD OF THE INVENTION

The present invention relates generally to absorbent articles intended for personal wear, and more particularly to an absorbent article configured for improved fit.

BACKGROUND OF THE INVENTION

Absorbent articles such as diapers, training pants, incontinence garments, and the like conventionally include a liquid permeable body-facing liner, a liquid impermeable outer cover, and an absorbent core (also referred to as an absorbent body or absorbent structure) formed separate from the outer cover and liner and disposed therebetween for taking in and retaining liquid (e.g., urine) exuded by the wearer.

Absorbent articles may be designed with extensible or elastic components that improve donning, fit during wear, and/or removal of the article from the wearer. In some of these absorbent articles, the outer cover and/or the liner may be somewhat stretchable and/or elastic to permit expansion of the article when necessary to provide a better fit on the wearer. For example, a child pulling on a pair of training pants typically pulls both upward on the pants and outward on the pants (e.g., at the waist) to widen the waist opening and pull the pants up over the buttocks and hips to the child's waist. Accordingly, an expansion force (i.e., a donning force) is applied to the article during donning to increase its dimensions.

One factor in reducing the risk of leakage from such pants is the quality of fit of the pants around the wearer's body and the magnitude of the retraction loading of the pants after the pants have been extended during donning. Ideally, the pants would be fully elastic, having a limited extension loading enabling the article to be very easily expanded and donned. The retraction loading of such an ideal article would be equal to or greater than the donning force required to expand the pants during donning. However, typical materials suitable for use in absorbent articles have different extension loadings and retraction loadings. The difference between the extension and retraction loading causes pants to be designed with either low extension loading and very little to no retraction loading, very high extension loading and satisfactory retraction loading, or a balanced extension loading and retraction loading which results in a narrow range of fit. Typically, an elastic waistband, elastic side panels, and elastic leg elements provide existing pants with a satisfactory extension loading and retraction loading around the wearer's waist and legs to provide good fit and prevent leakage.

Each layer of material of the absorbent article may contribute to the extension loading required for donning of the article and the retraction loading of the pants that determines the quality of fit against the body of the wearer. It is known to reduce the required extension loading of certain components of the pants (e.g., absorbent structure) to decrease the required extension loading of the assembled pants to make the pants easier to don. However, the design of such pants with improved donning (i.e., decreased extension loading) has included selection of pants components based solely on the extension loading properties, while the amount of retraction in the pants component has been overlooked. The resulting pants with reduced extension loading for improved donning results in pants having less retraction loading and a more loose fit against the body of the wearer. There is a need, therefore, to improve the construction of the stretchable absorbent article to increase the retraction loading to improve the fit of the article while maintaining the ease of donning of the article.

SUMMARY OF THE INVENTION

In one embodiment of the invention, a stretchable absorbent article generally has a longitudinal axis, a lateral axis, a front waist region, a back waist region, a crotch region extending longitudinally between and interconnecting the front and back waist regions, a length, and a width. The absorbent article generally comprises a liquid impermeable outer cover stretchable in at least one direction and a liner in opposed relationship with the outer cover and stretchable in at least one direction. At least one of the liner and the outer cover has a width substantially equal to the width of the absorbent article along the length thereof. An absorbent structure is disposed between the liner and the outer cover and extends from the crotch region to at least one of the front waist region and the back waist region of the article. The absorbent article has a retraction loading, an extension loading, and a ratio of retraction loading to extension loading as measured by an Absorbent Article Tensile Test. The ratio of retraction loading to extension loading of the absorbent article is greater than about 0.1 for a strain of approximately 10 percent as measured by said Absorbent Article Tensile Test.

In another embodiment of the invention, a stretchable absorbent article generally has a longitudinal axis, a lateral axis, a front waist region, a back waist region, a crotch region extending longitudinally between and interconnecting the front and back waist regions, a length, and a width. The article generally comprises a liquid impermeable outer cover that is elastic in at least one direction and a liner in opposed relationship with the outer cover and stretchable in at least one direction. At least one of the liner and the outer cover has a width substantially equal to the width of the absorbent article along the length thereof. An absorbent structure is disposed between the liner and the outer cover and extends from the crotch region to at least one of the front waist region and the back waist region of the article. The outer cover has a retraction loading, an extension loading, and a ratio of retraction loading to extension loading as measured by a Material Elongation Tensile Test. The ratio of retraction loading to extension loading being greater than about 0.15 for a strain of approximately 10 percent.

In yet another embodiment of the invention, the stretchable absorbent article has a longitudinal axis, a lateral axis, a front waist region, a back waist region, a crotch region extending longitudinally between and interconnecting the front and back waist regions, a length, and a width. The article generally comprises a liquid impermeable outer cover that is elastic in at least one direction. The outer cover generally comprises at least one rubber film. A liner in opposed relationship with the outer cover and stretchable in the at least one direction. At least one of the liner and outer cover encircles a waist of a wearer of the article during use. An absorbent structure is disposed between the liner and the outer cover and extends from the crotch region to at least one of the front waist region and the back waist region of the article.

Other features of the invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE INVENTION

Figure 1:
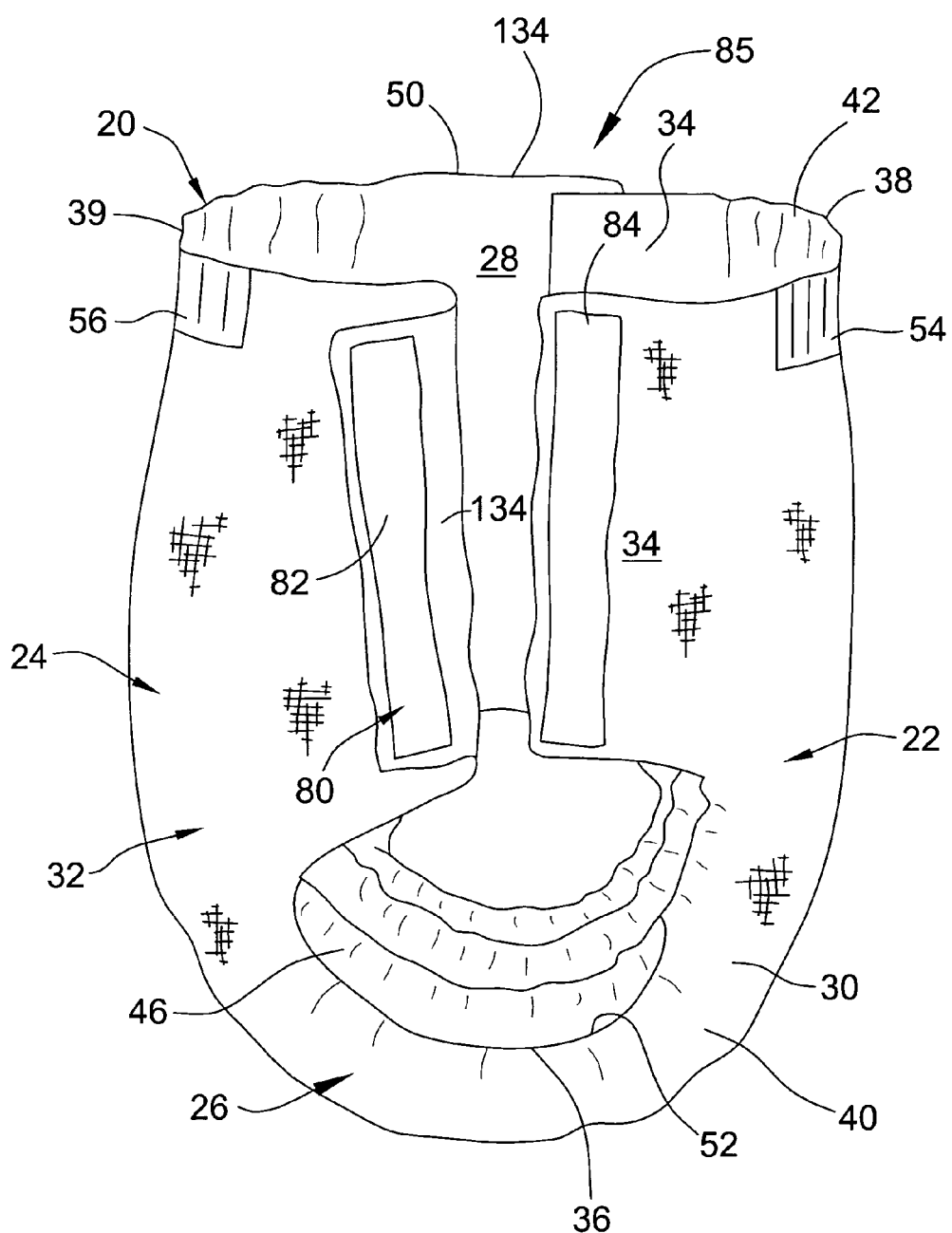
FIG. 1 is a perspective view of an absorbent article of the present invention shown in the form of a pair of training pants having a mechanical fastening system fastened on one side of the training pants and unfastened on the opposite side thereof.

Referring now to the drawings and in particular to FIG. 1, an absorbent article of the present invention is representatively illustrated therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

Figure 2:
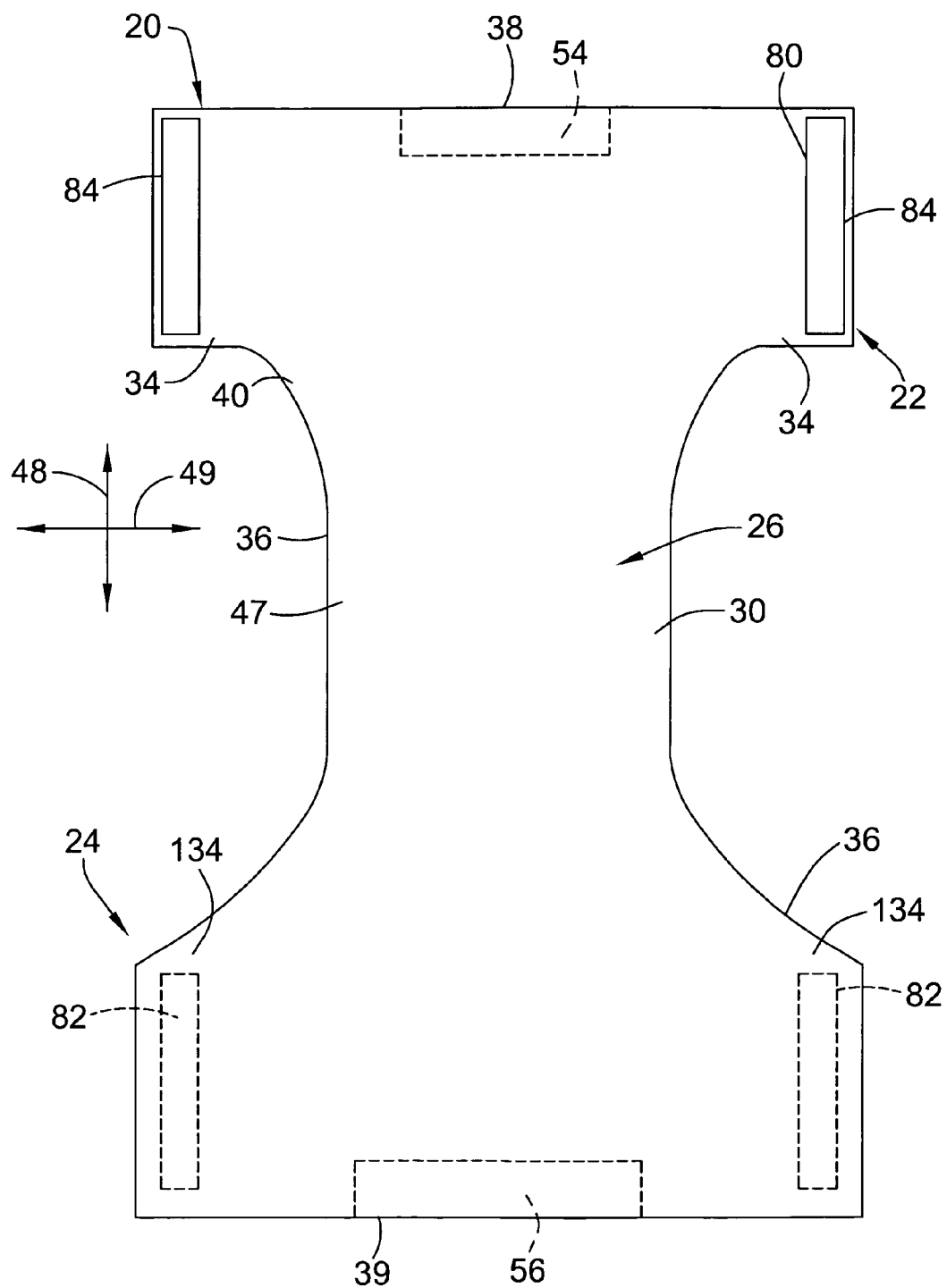
FIG. 2 illustrates a view of the training pants of FIG. 1 with the pants in an unfastened, unfolded and laid flat condition, and showing the surface of the training pants that faces away from the wearer.
Figure 3:
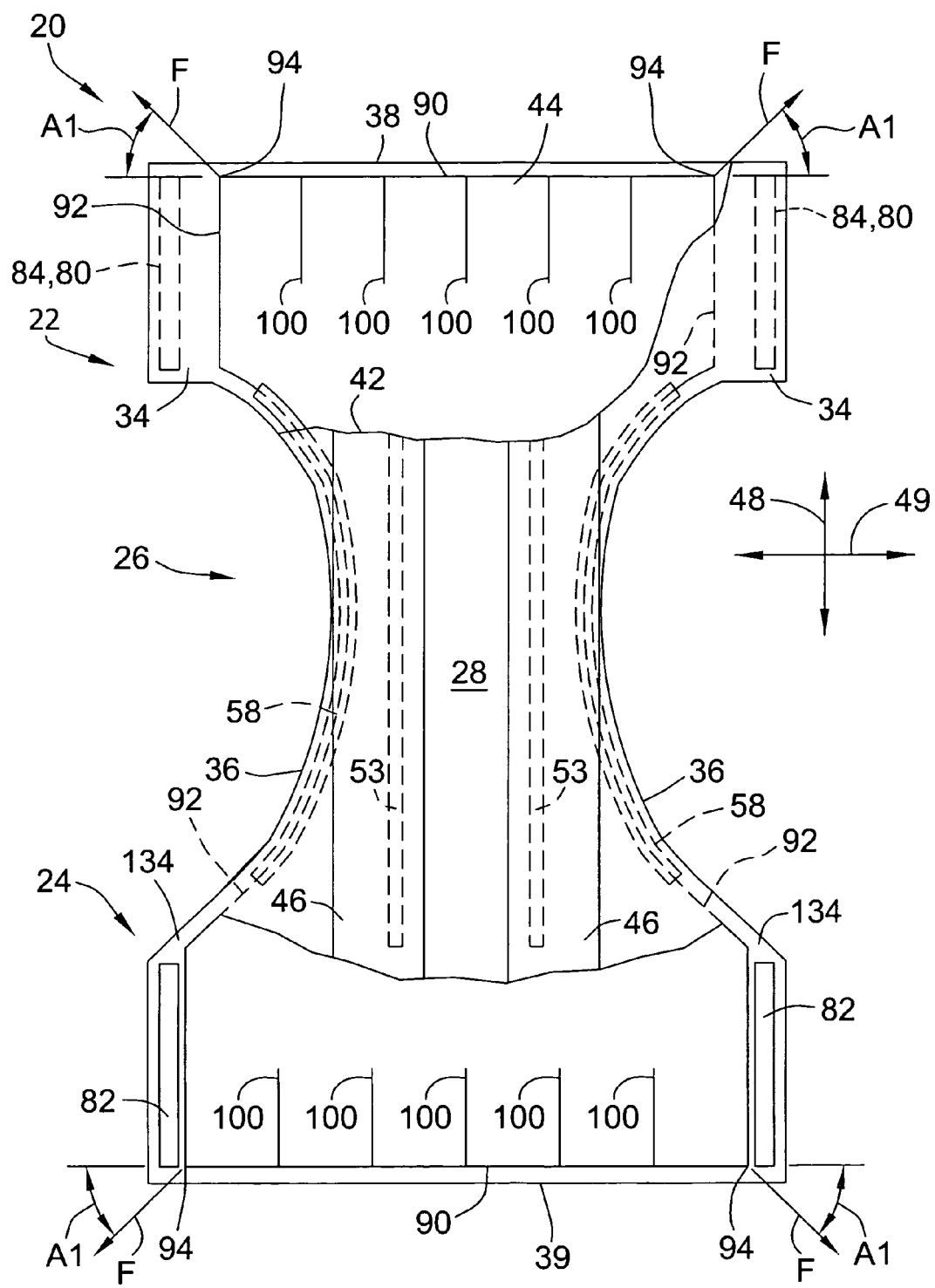
FIG. 3 illustrates a view similar to FIG. 2 showing the surface of the training pants that faces the wearer when worn and with portions cut away to show underlying features.

The pair of training pants 20 is illustrated in FIG. 1 in a partially fastened condition. The pants 20 define a longitudinal direction 48 of the pants (e.g. of the article) and a lateral direction 49 perpendicular to the longitudinal direction as shown in FIGS. 2 and 3. The pants 20 further define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The pants 20 also define an inner surface 28 adapted in use (e.g., positioned relative to the other components of the pants 20) to be disposed toward the wearer, and an outer surface 30 opposite the inner surface. The front and back waist regions 22, comprise those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. With additional reference to FIGS. 2 and 3, the pair of training pants 20 has a pair of laterally opposite side edges 36 and a pair of longitudinally opposite waist edges (broadly, longitudinal ends), respectively designated front waist edge 38 and back waist edge 39.

The illustrated pants 20 comprises an absorbent assembly, generally indicated at 32, and a fastening system for securing the pants in a three-dimensional pants configuration. The absorbent assembly 32 is illustrated as having an hourglass shape. However, it is contemplated that the absorbent assembly 32 may have other shapes (e.g., rectangular, T-shaped, I-shaped, and the like) without departing from the scope of this invention.

The absorbent assembly 32 comprises an outer cover 40 and a bodyside liner 42 (FIGS. 1 and 3) attached to the outer cover 40 in a superposed (opposed) relation therewith by adhesives, ultrasonic bonds, thermal bonds, pressure bonds, or other conventional techniques. The liner 42 is suitably joined to the outer cover 40 along at least a portion of the longitudinal ends of the pants 20 and at least in part defines the inner surface 28 of the article. The absorbent assembly 32 also comprises an absorbent structure 44 (FIG. 3) disposed between the outer cover 40 and the bodyside liner 42 for absorbing liquid body exudates exuded by the wearer and a pair of containment flaps 46 secured to the bodyside liner 42 for inhibiting the lateral flow of body exudates.

The pants 20 have a pair of laterally opposite front side portions 34 extending outward from the absorbent assembly 32 at the front waist region 22 and a pair of laterally opposite back side portions 134 extending outward from the absorbent assembly at the back waist region 24. In the illustrated embodiment, the pants 20 are suitably formed as what is referred to herein as a "one-piece" design. The term "one-piece" refers to the side portions 34, 134 being integrally formed with the bodyside liner 42 and/or the outer cover 40, i.e., the liner and/or outer cover have a width substantially equal to the width of the pants 20 along the length of the pants at the front and back waist regions 22, 24 to encircle the waist of the wearer during use. More suitably, the pants are formed as a "one-piece" elastic pants 20 for improved retraction loading and fit as described in further detail later herein.

With the training pants 20 in the fastened position as partially illustrated in FIG. 1, the front and back waist regions are connected together by the fastening system 80 to define the three-dimensional pants configuration having a waist opening 50 and a pair of leg openings 52. The front and back side portions 34 and 134, upon wearing of the pants 20, thus comprise the portions of the training pants 20 which are positioned on the hips of the wearer. The front and back waist edges 38 and 39 (e.g. longitudinal ends) of the training pants 20 are configured to encircle the waist of the wearer to define the waist opening 50 (FIG. 1) of the pants.

As illustrated in FIG. 3, a flap elastic member 53 can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges, and can extend longitudinally along the entire length of the absorbent assembly 32 or may extend only partially along the length thereof. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may comprise a front waist elastic member 54 (FIG. 2), a rear waist elastic member 56, and leg elastic members 58 (FIG. 3), as are known to those skilled in the art. The waist elastic members 54 and 56 may be operatively joined to the outer cover 40 and/or the bodyside liner 42 adjacent the longitudinal ends 38, 39. The leg elastic members 58 may be operatively joined to the outer cover 40 and/or the bodyside liner 42 along the opposite side edges generally at the crotch region 26 of the training pants 20.

The flap elastic members 53, the waist elastic members 54 and 56, and the leg elastic members 58 can be formed of any suitable elastic material. Suitable elastic materials for the flap, waist and leg elastic members comprise sheets, threads, strands, or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may comprise a plurality of dry-spun coalesced multifilament spandex elastomeric threads sold under the trade name LYCRA and available from Invista, Inc. of Wilmington, Del., U.S.A.

The fastening system 80 of the illustrated embodiment comprises laterally opposite first fastening components 82 attached to the side portions 134 and adapted for refastenable engagement to corresponding laterally opposite second fastening components 84 attached to the side portions 34. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 comprise loop fasteners and the second fastening components 84 comprise complementary hook fasteners. Alternatively, the first fastening components 82 can comprise hook fasteners and the second fastening components 84 can comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. When engaged, the fastening components 82, 84 of the illustrated aspect define refastenable engagement seams 85 (FIG. 1). Suitable fastening systems are also disclosed in PCT Patent Application WO 00/37009 published Jun. 29, 2000 by A. Fletcher et al. and U.S. Pat. No. 6,645,190 issued Nov. 11, 2003 to Olson et al. which are incorporated herein by reference to the extent they are consistent herewith.

The outer cover 40 is suitably constructed at least in part of a liquid impermeable material. More suitably, the outer cover 40 is constructed to be liquid impermeable and stretchable, and even more suitably the outer cover is constructed to be liquid impermeable and elastic. As used herein, the term "stretchable" refers to a material that may be extensible or elastomeric. That is, the material may be extended, deformed or the like, without breaking, and may or may not significantly retract after removal of an extending force. The term "elastic" as used in reference to the outer cover construction, refers to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent deformation or the material does not exhibit a significant retractive force.

In particular, the elastic outer cover may be elongated/extended or stretched in at least one direction without breaking by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally more suitable that the elastic outer cover be capable of being elongated by at least 100%, and more suitably by at least 200%, of its relaxed length and recover at least 30% and more suitably at least 50% of its elongation upon release of a stretching, biasing force, within about one minute.

The outer cover 40 in one embodiment suitably comprises a liquid impermeable elastic film or sheet (e.g., as opposed to a woven or non-woven web of individual elastic strands) that provides an increased amount of retraction loading following elongation, and improved fit of the pants. For example, in a particularly suitable embodiment the outer cover 40 is constructed at least in part of one or more layers of natural rubber (e.g., latex rubber, dry natural rubber, or any other type of natural rubber) that provides a high retraction loading. In other particularly suitable embodiments, the outer cover 40 may be constructed at least in part of one or more layers of synthetic rubber (e.g., neoprene, EPDM rubber, Buna-N (Nitrile), VITON rubber, etc.). Other suitable liquid impermeable elastic materials having a high retraction loading following elongation include KRATON elastomers (available from Kraton Polymers of Houston, Tex.), HYTREL elastomers (available from Invista, Inc. of Wilmington, Del.), ESTANE elastomeric polyurethanes (available from Noveon of Cleveland, Ohio), or PEBAX elastomers (available from AtoChem located in Philadelphia, Pa.).

As an example, the outer cover 40 may suitably comprise a layer of latex rubber (commercially available from MSC Industrial Supply Co. of Mableton, Ga.) having a thickness of about 0.006 inch (0.15 mm). It is understood, however, that the liquid impermeable elastic material of the outer cover is commercially available from other suppliers and may have a thickness greater or less than the above thickness, such as in the range of about 0.01 mm to about 2.0 mm (about 0.0004 inch to about 0.078 inch) or any other range, without departing from the scope of this invention. It is understood that the elastic properties (e.g., elongation and recovery percentages, retraction loading, extension loading, etc.) of the outer cover 40 may be affected by the specific material properties (e.g., molecular structure, chemical properties, manufacturing processes, etc.) of the material selected for the outer cover and that the elastic properties of the outer cover may be changed with or without changing the thickness of the outer cover.

In addition to the elongation and recovery capabilities set forth above, the outer cover 40 of the present invention suitably comprises a material having an increased retraction load when compared to existing outer covers that may be stretchable, extendable, and/or elastic. For example, Experiment 1 described later herein, compares the performance characteristics of one suitable material for the outer cover 40 (latex rubber—Sample 2) with a known elastic outer cover material (laminated stretchable film with non-woven web—Sample 3). As shown in Table 2, the elastic outer cover material of one embodiment of the present invention (Sample 2) has a retraction loading greater than the retraction loading of the prior art outer cover material (Sample 3) throughout the range of strain points included in the experiment. Further, the retraction loading of the elastic outer cover material of the present invention (Sample 2) has a retraction loading at least two times the value of the retraction loading of the prior art material (Sample 3) across the range of strain points of the material. The increased retraction loading of the outer cover 40 provides the pants 20 with improved fit and reduced leakage.

The outer cover 40 may be further constructed of additional material layers (i.e., in addition to the liquid impermeable elastic material having a relatively high retraction loading upon elongation thereof). For instance, the outer cover 40 may comprise a laminate of a natural or synthetic rubber inner layer and an outer layer comprised of a generally cloth-like texture non-woven material. In a particularly suitable embodiment, the outer layer material is elastic so that the elasticity of the rubber inner layer is not inhibited. The outer layer and inner layer of such an embodiment may be suitably joined together by a laminate adhesive, ultrasonic bonds, thermal bonds, pressure bonds or the like. Suitable laminate adhesives, which can be applied continuously or intermittently as beads, a spray, parallel swirls, or the like, can be obtained from Bostik Findley Adhesives, Inc., of Wauwautosa, Wis., U.S.A., or from National Starch and Chemical Company, Bridgewater, N.J. U.S.A. One example of a suitable outer layer material is a 20 gsm (grams per square meter) spunbond polyolefin non-woven web. Examples of suitable cloth-like outer layer materials are spunbond-meltblown fabrics, spunbond-meltblown-spunbond fabrics, spunbond fabrics, or laminates of such fabrics with films, foams, or other nonwoven webs.

The outer cover 40 of the pants 20 has an extension loading (i.e., the amount of force required to elongate a material or article a given amount) and retraction loading (i.e., the amount of bias tending to retract the elongated material or article following elongation of the material or article a given amount), and a ratio of the retraction loading to the extension loading that may be measured by a Material Elongation Tensile Test as set forth below. In one embodiment, the ratio of retraction loading to extension loading of the outer cover 40 is suitably greater than about 0.15 for a strain (e.g., elongation) of approximately 10 percent as measured by the Material Elongation Tensile Test, and more suitably in the range of about 0.15 to about 0.5 for a strain of approximately 10 percent. Alternatively, or additionally, the ratio of retraction loading to extension loading of the outer cover 40 may be greater than about 0.35 for a strain of approximately 20 percent as measured by the Material Elongation Tensile Test, and more suitably in the range of about 0.35 to about 0.7 for a strain of approximately 20 percent.

Also alternatively, or additionally, the ratio of retraction loading to extension loading of the outer cover 40 may be greater than about 0.45 for a strain of approximately 30 percent as measured by the Material Elongation Tensile Test, and more suitably in the range of about 0.45 to about 0.7 for a strain of approximately 30 percent. Further alternatively, or additionally, the ratio of retraction loading to extension loading of the outer cover 40 may be greater than about 0.60 for a strain of approximately 40 percent as measured by the Material Elongation Tensile Test, and more suitably in the range of about 0.6 to about 0.8 for a strain of approximately 40 percent. The ratio of retraction loading to extension loading of the outer cover 40 may alternatively, or additionally, be greater than about 0.85 for a strain of approximately 50 percent as measured by the Material Elongation Tensile Test, and more suitably in the range of about 0.85 to about 0.9 for a strain of approximately 50 percent.

Experiment 1

Figure 4:
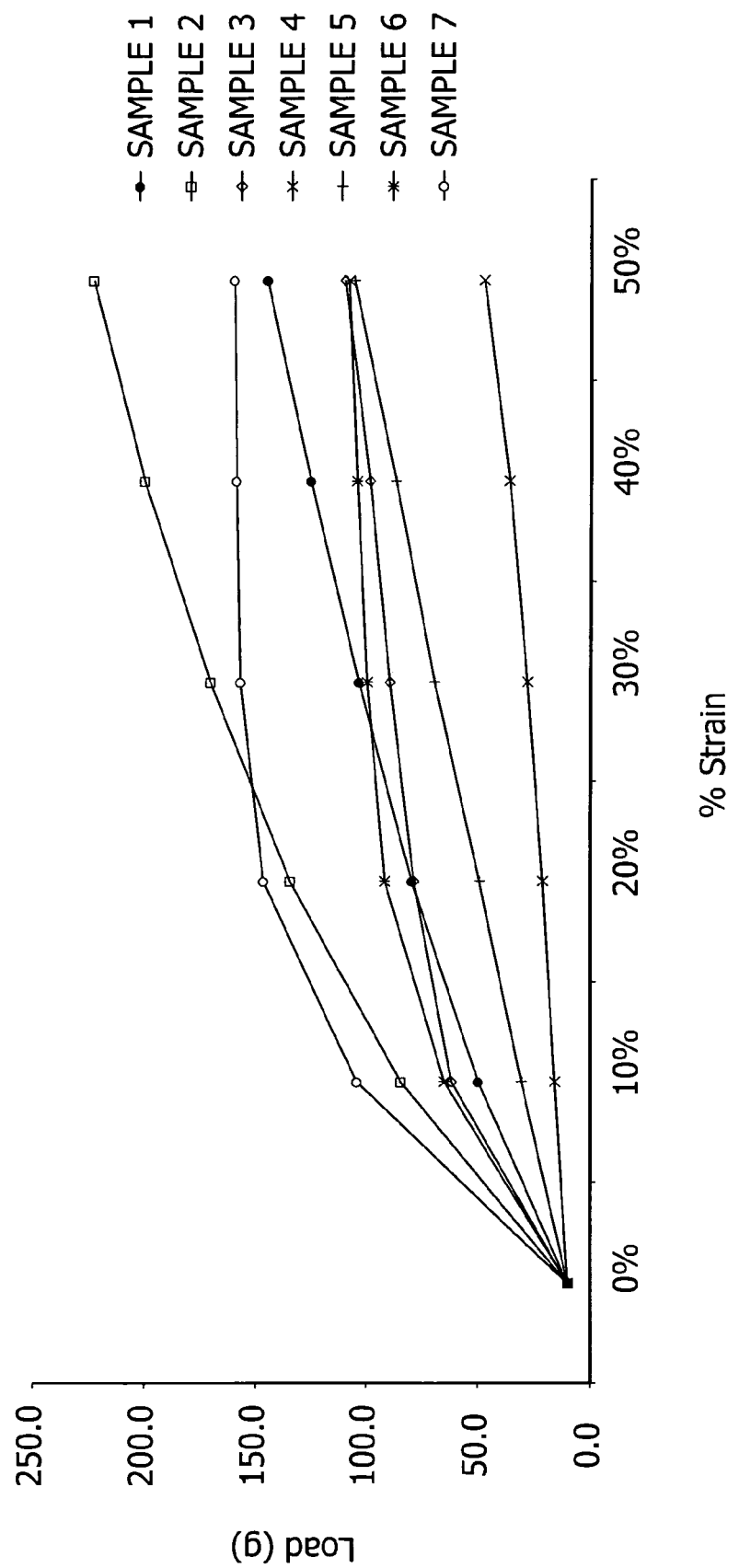
FIGS. 4-6 are plots of data obtained in a first experiment.
Figure 5:
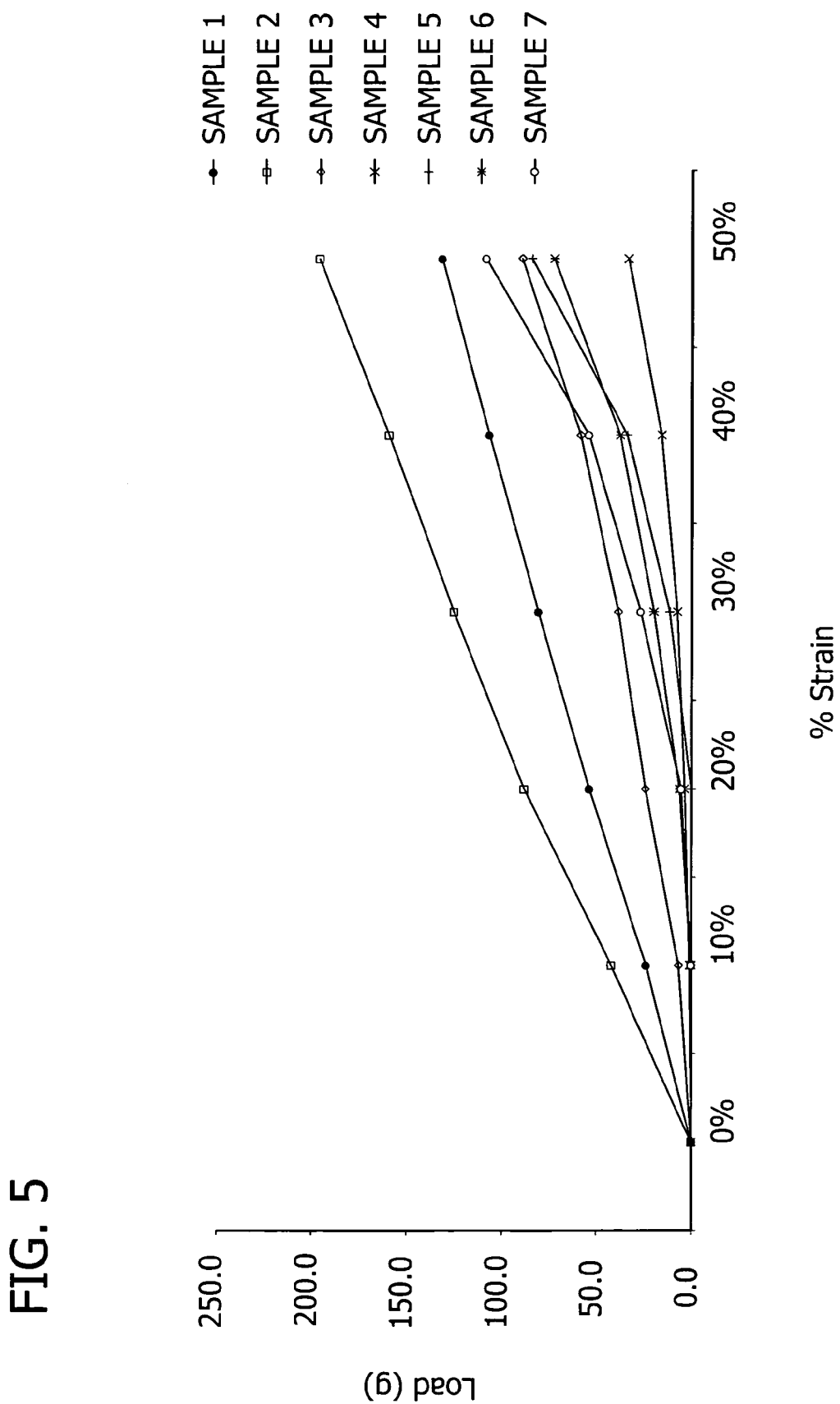
Figure 6:
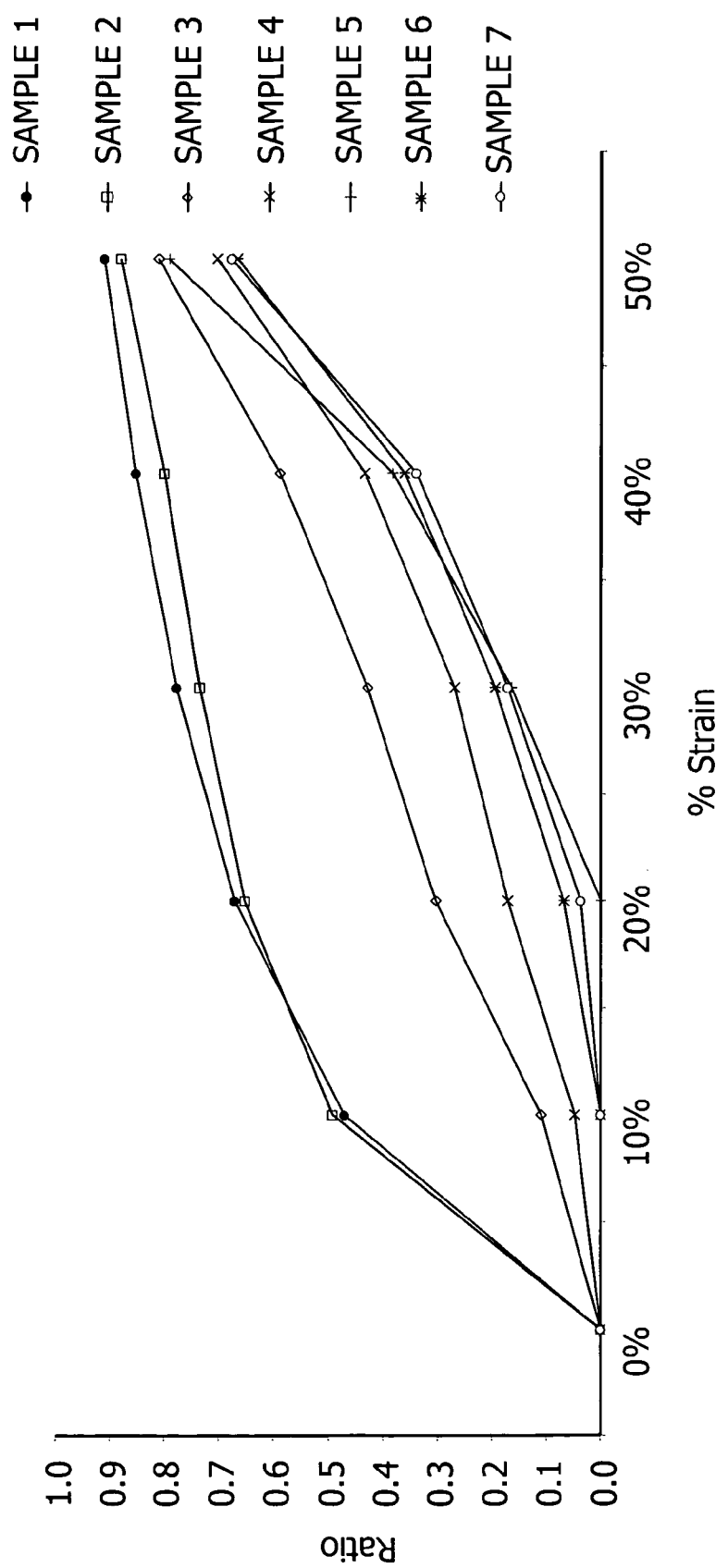

A Material Tensile Test, as described later herein, was used to test the extension properties and retraction properties of various elements of the pants to determine which elements provide suitable retraction loadings. All test samples were 1 inch×5 inches (2.5 cm×12.7 cm) strips of material. The tensile force applied to each sample during test was directed in the longitudinal direction of each sample. The results of Experiment 1 are shown in FIGS. 4-6 and provided in Tables 1-3 below.

Sample 1 was a LYCRA laminate waist elastic material. The material comprised 9 strands of 540d LYCRA material applied at 300 percent elongation and sandwiched between two 0.3 osy (31 gsm) sheath/core 30% polyethylene/70% polypropylene spunbond material.

Sample 2 was a latex rubber outer cover material that comprised 0.006 inch (0.15 mm) gauge thickness. The latex rubber material is available in sheets as part number 31934748 from MSC Industrial Supply Co. of Mableton, Ga.

Sample 3 was an outer cover material comprising a laminated stretchable film and non-woven web, the laminate being produced with the following materials and processes. A film layer filler concentrate comprised of 75% calcium carbonate was dispersed into a polymeric carrier resin. The calcium carbonate, available from Omya, Inc. North America of Proctor, Vt., and designated as 2SST, has an average particle size of 2 microns with a top cut of 8-10 microns and a coating of approximately 1% stearic acid. The polymeric carrier resin which comprises 25% of the blend was a DOWLEX 2517 LLDPE resin supplied by Dow Chemical U.S.A. of Midland Mich. DOWLEX 2517 has a density of 0.917 g/cc (0.530 o/ci) and a melt index of 25. The 75/25 blend of calcium carbonate and LLPE resin was subsequently blended with 33% of SEPTON 2004 which is a SEPS based styrenic block copolymer to provide a final calcium carbonate concentration of 50.25% by weight. The SEPTON resin is available from Septon Company of America of Pasadena, Tex.

The formulation was formed into a film by casting onto a chill roll set to 38° C. (100° F.) at an unstretched basis weight of approximately 67 gsm (1.9 osy). The casting speed was 125 ft/minute (38.1 m/minute). The film was heated to a temperature of 47.5° C. (125° F.), stretched 3.9 times its original length using a machine direction orientor at a line speed of 493 ft/minute (150 m/minute). The film was retracted 0% resulting in a stretched basis weight of approximately 33 gsm (1.0 osy). As used herein, stretching 3.9 times means that a film which, for example, had an initial length of 1 meter if stretched 3.9 times would have a final length of 3.9 meters. The film was then annealed at a temperature of 42° C. (110° F.) across multiple rolls at a line speed of 493 ft/minute (150 m/minute).

The fibrous non-woven web for the outer cover material of Sample 3 was a 20 gsm (0.58 osy) spunbond web produced by BBA Materials Technology of Nashville, Tenn. with the trade name of Sofspan 120. The fibrous non-woven web was introduced into a nip of intermeshing grooved steel rolls at a velocity of 146.9 meters/min (482 ft/m) with the grooves in the rolls being concentric. Each groove was formed with a depth of 0.51 cm (0.200 inch) and with a peak to peak distance of 0.31 cm (0.125 inch) resulting in a maximum draw ratio of 3.4×. The spunbond was stretched to a draw of 2.6× or 160% in the cross direction (CD). The fibrous non-woven web was heated to a temperature of 93.3° C. (200° F.) while it passed subsequently under a hot air knife and through the temperature controlled nip between grooved rolls set to intermeshing engagement of 3.81 mm (0.15 inch). The spunbond was drawn 2% in the machine direction between the groove roll unit and the lamination unit causing the CD width to be necked in 5% (even though it had been stretched in the CD by the grooved rolls) to a new width of 50.80 cm (20 inches).

The outer cover material for Sample 3 was formed by lamination of the film and non-woven web using adhesive lamination with a slot die coater. HX9375-01 adhesive, produced by Bostik Findley corporation of Wauwautosa, Wis., was melted to a temperature of 177° C. (350° F.) and applied to the spunbond sheet with an add-on level of 1 gsm (0.03 osy).

The produced laminate for the outer cover material of Sample 3 was retracted 10% in the machine direction between the lamination unit and fourth roll in the annealing unit maintaining its width. The laminate was annealed and cooled using 4 temperature controlled rolls. The laminate with the film side in contact with the rolls was heated at 82° C. (180° F.) over two rolls and then cooled at 16° C. (60° F.) over the next two rolls to set the final machine and cross direction stretch material properties. Finally the laminate was transferred with minimal retraction to the winder for a final basis weight of 59 gsm (1.7 osy).

The bodyside liner of the composite comprised a 0.3 osy (10.2 gsm) polypropylene spunbond web that was creped 60% and necked 60%. The terms "creped" or "crepe" refer to a crinkled material or composite having bonded and unbonded areas. The creped material can be returned to approximately its original length by applying a mechanical stress, thus smoothing out the crinkled portions. "Necked" or "neck stretched" are interchangeable terms and refer to a method of elongating a non-woven fabric, generally in the longitudinal or machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244,482 to Hassenboehler Jr. et al.

Sample 4 was a bodyside liner material comprising a 0.60 osy (20.4 gsm) 85 percent sheath/core bicomponent spunbond material. Thermal Plastic Urethane (TPU) was the core and polyurethane was the sheath.

Sample 5 was a bodyside liner material comprising a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like.

Sample 6 was an absorbent structure material comprising a coform absorbent structure material with a target basis weight of about 425 gsm (12.3 osy) and a density of 0.31 g/cc (0.18 o/ci). Sample 6 had weakening elements in the form of three pairs of ¼ inch (6.4 mm) long slits that extended from the lateral side edges of the sample in the lateral direction. The slits of each pair extended from a respective lateral side edge of the sample and were longitudinally aligned such that ½ inch (12.7 mm) of absorbent material separated the slits of each pair. The pairs of slits were spaced approximately one inch (25.4 mm) apart in the longitudinal direction of the sample with each of the two outer pairs of slits being located approximately 1.5 inches (38.1 mm) from the closest longitudinal edge margin of the sample and the middle slit being located approximately on the longitudinal centerline of the sample (i.e., approximately 2.5 inches (63.5 mm) from both longitudinal edge margins of the sample).

Sample 7 was an absorbent structure material similar to Sample 6 but without weakening elements or slits.

Plots comparing the test results of the first experiment are provided in FIGS. 4-6 and Tables 1-3 below. Specifically, FIG. 4 and Table 1 provide the extension loading (referred to as "Load" in the plot) at various strains (e.g., elongation) for each of the tested samples; FIG. 5 and Table 2 provide the retraction loading at various strains for each sample; and FIG. 6 and Table 7 provide the ratio of the retraction loading to the extension loading at various strains for each sample. The data provided in FIG. 6 for the retraction loading/extension loading ratios of the tested materials can be used to select the materials of a suitable embodiment of the training pants that has a higher retraction loading and an improved fit to the wearer. For example, the Sample 2 (latex outer cover) material has a higher ratio across the range of strains than the material of Sample 3 comprising conventional outer cover material. As shown in FIGS. 5 and 6, the increase in the retraction loading/extension loading ratio for Sample 2 results from the retraction loading of Sample 2 being closer to the extension loading across the range of strains in the experiment.

FIG. 6 also illustrates that Sample 6 including weakening elements in the absorbent material has a higher ratio of retraction loading to extension loading than Sample 7 that did not have weakening elements. As shown in FIG. 4, Sample 6 having slits oriented perpendicular to the tensile force required less extension loading than Sample 7 to produce the same amount of percent strain or elongation. While Sample 6 had slightly less retraction loading than Sample 7 (see FIG. 5), the more significant decrease in the extension loading is the dominant factor resulting in the increase of the ratio of retraction loading to extension loading shown in FIG. 6. Accordingly, pants constructed of the material of Sample 6 having a decreased extension loading would allow other materials (e.g., the outer cover) having a higher retraction loading to comprise a larger portion of the overall extension loading of the pants. Therefore, the absorbent of Sample 6 with weakening elements would be preferable over the Sample 7 material without weakening elements so that the absorbent material used in the pants would utilize less donning extension loading. The decrease in donning extension loading may allow other more efficient elastic materials (e.g., outer cover) to contribute greater donning extension loading and further contribute higher retraction loading without exceeding the maximum donning or extension loading for the article. Ultimately, the efficiency or uniformity of the extension loading versus retraction loading of the pant design of the present invention has been increased without increasing the amount of loading required to extend and don the pant.

TABLE 1

Material Extension Loading (grams)

|  | Strain 0% | Strain 10% | Strain 20% | Strain 30% | Strain 40% | Strain 50% |
| --- | --- | --- | --- | --- | --- | --- |
| Sample 1 | 10.0 | 49.5 | 79.7 | 103.4 | 124.6 | 144.2 |
| Sample 2 | 10.0 | 84.3 | 134.1 | 170.1 | 199.3 | 222.5 |
| Sample 3 | 10.0 | 61.5 | 78.7 | 89.4 | 98.3 | 109.5 |
| Sample 4 | 10.0 | 15.7 | 21.0 | 27.8 | 35.8 | 46.9 |
| Sample 5 | 10.0 | 30.4 | 49.2 | 69.1 | 86.7 | 105.5 |
| Sample 6 | 10.0 | 64.9 | 91.7 | 99.9 | 104.1 | 107.7 |
| Sample 7 | 10.0 | 104.3 | 146.2 | 156.4 | 158.1 | 159.1 |

TABLE 2

Material Retraction Loading (grams)

|  | Strain 0% | Strain 10% | Strain 20% | Strain 30% | Strain 40% | Strain 50% |
| --- | --- | --- | --- | --- | --- | --- |
| Sample 1 | 0.0 | 23.3 | 53.5 | 80.2 | 106.3 | 131.5 |
| Sample 2 | 0.0 | 41.5 | 87.6 | 125.0 | 159.3 | 195.7 |
| Sample 3 | 0.0 | 6.7 | 23.9 | 38.4 | 58.0 | 88.9 |
| Sample 4 | 0.0 | 0.7 | 3.6 | 7.5 | 15.5 | 33.1 |
| Sample 5 | 0.0 | 0.0 | 0.0 | 11.2 | 33.2 | 83.6 |
| Sample 6 | 0.0 | 0.0 | 6.1 | 19.5 | 37.5 | 72.0 |
| Sample 7 | 0.0 | 0.0 | 5.3 | 26.6 | 53.7 | 108.1 |

TABLE 3

Retraction Loading/Extension Loading Ratio

|  | Strain 0% | Strain 10% | Strain 20% | Strain 30% | Strain 40% | Strain 50% |
| --- | --- | --- | --- | --- | --- | --- |
| Sample 1 | 0.0 | 0.5 | 0.7 | 0.8 | 0.9 | 0.9 |
| Sample 2 | 0.0 | 0.5 | 0.7 | 0.7 | 0.8 | 0.9 |
| Sample 3 | 0.0 | 0.1 | 0.3 | 0.4 | 0.6 | 0.8 |
| Sample 4 | 0.0 | 0.0 | 0.2 | 0.3 | 0.4 | 0.7 |
| Sample 5 | 0.0 | 0.0 | 0.0 | 0.2 | 0.4 | 0.8 |
| Sample 6 | 0.0 | 0.0 | 0.1 | 0.2 | 0.4 | 0.7 |
| Sample 7 | 0.0 | 0.0 | 0.0 | 0.2 | 0.3 | 0.7 |

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastic. Suitable elastic materials for construction of the bodyside liner 42 can include non-woven elastic webs, meltblown or spunbond elastomeric fibrous webs, as well as combinations thereof. Examples of suitable elastic materials include KRATON elastomers (available from Kraton Polymers of Houston, Tex.), HYTREL elastomers (available from Invista, Inc. of Wilmington, Del.), ESTANE elastomeric polyurethanes (available from Noveon of Cleveland, Ohio), or PEBAX elastomers (available from AtoChem located in Philadelphia, Pa.).

As an additional example, in one aspect the bodyside liner 42 may suitably comprise a non-woven, spunbond polypropylene fabric composed of about 2 to 3 denier fibers formed into a web having a basis weight of about 12 gsm which is necked approximately 60 percent. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials can be extensible biaxially stretchable materials, such as a neck stretched/creped spunbond. The bodyside liner 42 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both references which are herby incorporated by herein by reference.

The liner 42 can suitably be stretched, laterally and/or longitudinally, by at least 30% (to at least 130% of an initial (unstretched) width and/or length of the liner 42). More suitably, the liner 42 can be stretched laterally and/or longitudinally, by at least 50% (to at least 150% of the unstretched width or length of the liner 42). Even more suitably, the liner 42 can be stretched, laterally and/or longitudinally, by at least 100% (to at least 200% of the unstretched width or length of the liner 42).

While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. One suitable type of fluff is identified with the trade designation CR 1654, available from U.S. Alliance of Childersburg, Ala., USA, and is a bleached, highly absorbent sulfate wood pulp containing primarily soft wood fibers.

The materials may be formed into a web structure by employing various conventional methods and techniques. For example, the absorbent structure 44 may be formed by a dry-forming technique, an air forming technique, a wet-forming technique, a foam-forming technique, or the like, as well as combinations thereof. Methods and apparatus for carrying out such techniques are well known in the art. Furthermore, the absorbent structure 44 may itself encompass multiple layers in a Z-direction (e.g., thickness) of the absorbent structure. Such multiple layers may take advantage of differences in absorbent capacity, such as by placing a lower absorbent capacity material layer closer to the liner 42 and a higher absorbent capacity material closer to the outer cover 40. Likewise, discrete portions of a single-layered absorbent structure may encompass higher capacity absorbents, and other discrete portions of the structure may encompass lower capacity absorbents.

Superabsorbent material is suitably present in the absorbent structure in an amount of from about 0 to about 90 weight percent based on total weight of the absorbent structure. The absorbent structure may suitably have a density within the range of about 0.10 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, SXM 9394, and Favor 9543 are suitable superabsorbent materials available from Degussa Superabsorbers of Germany.

After being formed or cut to a desired shape, the absorbent structure 44 may be wrapped or encompassed by a suitable wrap (not shown) that aids in maintaining the integrity and shape of the absorbent structure.

The absorbent structure 44 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In a particularly suitable embodiment, the absorbent structure 44 is stretchable so as not to inhibit the stretchability of other components to which the absorbent structure may be adhered, such as the outer cover 40 and bodyside liner 42. More suitably, the bodyside liner 42, the outer cover 40, and the absorbent structure 44 are each stretchable so that the absorbent structure allows for increased stretchability of the absorbent article as a whole. That is, non-stretchable absorbent structures 44 tend to inhibit stretching of the outer cover 40 and liner 42, even where the outer cover and liner are stretchable. A stretchable absorbent structure 44 allows the outer cover 40 and liner 42 to more readily stretch, thereby increasing the overall stretchability (and ease of stretching) the entire article.

For this purpose, the absorbent structure 44 material can include elastic fibers in an amount which is at least a minimum of about 2 wt %. The amount of elastic fibers can alternatively be at least about 3 wt %, and can optionally be at least about 5 wt % to provide improved performance. In addition, the amount of elastic fibers can be not more than about 60 wt %. Alternatively, the amount of elastic fibers can be not more than about 45 wt %, and optionally, can be not more than about 30 wt % to provide improved benefits. The elastic fiber content may impact the absorbent structure 44 stretchability and structural stability without excessively degrading the physical properties or the liquid-management properties of the absorbent structure. An absorbent structure 44 comprising an excessively low proportion of elastic fibers may be insufficiently stretchable, and one with an excessively high proportion of elastic fibers may exhibit an excessive degradation of its absorbent characteristics, such as poor intake, poor distribution and poor retention of liquid.

The absorbent structure 44 in one particularly suitable embodiment comprises an elastic coform material. Such materials are described for instance in U.S. Pat. Nos. 6,231, 557 B1 and 6,362,389 B1, which are each incorporated by reference herein. In particular aspects, the elastic coform material can have an overall coform basis weight which is at least a minimum of about 50 g/m$^2$. The coform basis weight can alternatively be at least about 100 g/m$^2$ and can optionally be at least about 200 g/m$^2$ to provide improved performance. These values can provide the absorbent structure 44 with the desired stretchability and structural stability without excessively degrading the physical properties or the liquid-management characteristics of the absorbent structure.

Other examples of suitable elastic absorbent structures are described in international patent application WO 03/051254 and U.S. Pat. Nos. 5,964,743, 5,645,542, 6,231,557, and 6,362,389 B1, each of which are incorporated by reference herein.

In some embodiments a surge management layer (not shown) may be located adjacent the absorbent structure 44 (e.g., between the absorbent structure and the liner 42) and attached to various components of the article 20 such as the absorbent structure and/or the bodyside liner by methods known in the art, such as by adhesive, ultrasonic or thermal bonding. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure 44. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein.

The donning force of an absorbent article refers herein to the extension force (loading) applied to the article to properly don the article on the wearer. The donning force typically comprises a pulling force applied by the wearer (e.g., via the wearer pulling upward and/or outward on the article), and may further comprise an expansion force applied by the wearer's body to the article to increase the dimensions of the article so as to accommodate the shape and size of the wearer. For example, with reference to the training pants 20, the donning force is the force (indicated representatively as F in FIG. 3) applied to the pants (e.g., at the waist opening) by a child (or caregiver) to pull the pants up to the child's waist. This typically comprises sufficient force not only to lift the pants 20 upward but also to expand the waist opening 50 of the pants outward. Additionally, as the pants 20 are pulled up over the child's thighs, buttocks and hips, the child's body may apply additional donning force (e.g., an expansion force) to the pants to expand the waist opening 50 and leg openings 52 of the pants.

The magnitude and direction of application of the donning force F can vary based on the size and construction of the absorbent article being donned, and/or on the donning tendencies of the wearer (i.e., the manner in which a wearer typically dons a garment, such as one foot first, both feet first, pulling at the front and back or at the sides of the article, donning while standing, or sitting, etc.). However, it is believed that the donning force, particularly for absorbent articles 20 such as training pants and incontinence products that are donned about the hips and waist of a wearer, is applied in a direction that defines an angle A1 (FIG. 3) of greater than zero degrees and less than 90 degrees with respect to the lateral direction 49 of the article. More specifically, it is believed that the donning forces for such absorbent articles 20 are more commonly in a direction that defines an angle A1 of greater than or equal to 30 degrees and less than 90 degrees relative to the lateral direction 49, and even more commonly in a direction than defines an angle A1 greater than or equal to 60 degrees and less than 90 degrees relative to the lateral direction.

In one embodiment, the absorbent structure 44 of the present invention is further configured to reduce the resistance to stretching of the absorbent article, particularly in the direction of application of the donning force F, so that a lower donning force is required to don the article 20 on the wearer. With particular reference to FIG. 3, the absorbent structure 44 may comprise at least one weakening element 100 disposed therein for weakening the absorbent structure to thereby substantially reduce the resistance of the absorbent structure to stretching in the direction of the applied donning force F. For example, in the illustrated embodiment the absorbent structure 44 has four weakening elements 100, one adjacent to each of the corner regions 94 of the absorbent structure (i.e., adjacent to each longitudinal end 90 and corresponding adjacent lateral side edge 92 of the absorbent structure) in the front and back waist regions 22, 24 of the article.

It is contemplated, however, that weakening elements 100 may have other shapes (e.g., curved) and may be elements other than continuous slits (e.g., voids, apertures, etc.) without departing from the scope of this invention. Also, the weakening elements may be disposed only in the front waist region 22 of the article 20, or only in the back waist region 24 thereof, without departing from the scope of the invention. By way of example, the weakening elements may be constructed similar to the weakening elements described in U.S. patent application Ser. No. 10/835,638 filed on Apr. 30, 2004 by Sperl et al. and U.S. patent application Ser. No. 11/026,423 filed on Dec. 30, 2004 by Sperl et al., both references being incorporated herein by reference.

The pants 20 of the present invention have been designed to have components that provide an increased amount of retraction loading upon elongation of the pants so that the pants provide an improved fit (e.g., more conforming and snug) that prevents leakage from the pants, while maintaining a desirable low donning force required to elongate and don the pants. Less reliance is thus placed on the front waist elastic member 54, rear waist elastic member 56, and leg elastic members 58 (FIG. 3) to provide the overall pants retraction loading that holds the pants against the wearer's body.

In particular, the pants 20 have an extension loading (i.e., the amount of force required to elongate a material or article a given amount) and retraction loading (i.e., the amount of bias tending to retract the elongated material or article following elongation of the material or article a given amount), and a ratio of retraction loading to extension loading as measured by an Absorbent Article Tensile Test set forth below. In one embodiment, the pants 20 (broadly, the absorbent article) have a ratio of retraction loading to extension loading of greater than about 0.1 for a strain (e.g., elongation) of approximately 10 percent as measured by the Absorbent Article Tensile Test, and more suitably in the range of about 0.1 to about 0.15 for a strain of approximately 10 percent.

The pants 20 may alternatively, or additionally, have a ratio of retraction loading to extension loading of at least about 0.2 for a strain of approximately 20 percent as measured by the Absorbent Article Tensile Test, and more suitably in the range of about 0.2 to about 0.4 for a strain of approximately 20 percent. In another embodiment, the pants 20 have alternatively, or additionally, have a ratio of retraction loading to extension loading of at least about 0.35 for a strain of approximately 30 percent as measured by the Absorbent Article Tensile Test, and more suitably in the range of about 0.35 to about 0.6 for a strain of approximately 30 percent. The pants 20 may alternatively, or may additionally, have a ratio of retraction loading to extension loading that is greater than about 0.53 for a strain of approximately 40 percent as measured by the Absorbent Article Tensile Test, and more suitably in the range of about 0.55 to about 0.7 for a strain of approximately 40 percent.

Also alternatively, or additionally, the pants 20 may have a ratio of retraction loading to extension loading of greater than about 0.85 for a strain of approximately 50 percent as measured by the Absorbent Article Tensile Test, and more suitably in the range of about 0.85 to about 0.91 for a strain of approximately 50 percent. The pants 20 constructed according to the present invention and having the above-noted performance characteristics provide an increased amount of retraction loading without a significant increase in extension loading that would otherwise require an undesirably high donning force to don the pants. Accordingly, the pants provide an improved fit (e.g., comfort, conformability and snugness) while staying relatively easy to extend during donning.

Experiment 2

A second experiment was performed using an Absorbent Article Tensile Test, as described later herein, to test the overall extension and retraction loadings of a pair of training pants comprised of materials selected from Experiment 1. Two pants were tested in this experiment to determine the retraction loading and extension loading properties of each of the pants.

Pants 1 represented pants made in accordance with the present invention having materials selected to enhance the retraction loading of the pants to provide a better fit. Pants 1 included a waistband made of the LYCRA material of Sample 1 (reference to "Samples" herein being to the Samples of Experiment 1), leg elastics made of the LYCRA material of Sample 1, an outer cover made of latex rubber material of Sample 2, a bodyside liner made of the spunbond material of Sample 4, and an absorbent structure made of a coform absorbent material of Sample 6. The absorbent structure of Pants 1 had five longitudinal slits, 3 inches (75 mm) long and evenly spaced across the front waist region of the absorbent structure and five longitudinal slits, 3 inches (75 mm) long and evenly spaced across the back waist region of the absorbent structure.

The adhesive used to attach the outer cover and bodyside liner and the absorbent structure of Pants 1 comprised a hot melt adhesive available from Bostik-Findley Adhesive of Wauwautosa, Wis. and designated as A2525. Double-sided adhesive tape available from 3M Company of Minneapolis, Minn. and designated as No. 9509 was also used in the assembly of the pants.

Pants 1 was a one-piece stretchable pants design comprising the above-noted materials to provide an improved retraction loading of the pants. The pants construction was accomplished as follows:

1. The outer cover material was first cut into an hourglass shape.
2. The leg elastic laminate consisting of LYCRA strands and a sheath/core 30% polyethylene/70% polypropylene spunbond material facing were adhered to both lateral inside edges of the outer cover in the longitudinal center ⅓ of the article. The leg elastics were in the longitudinal center of the pants and oriented in the longitudinal direction having a lateral width of ½ inch (12 mm).
3. The waist elastic laminate consisting of LCYRA strands and spunbond facing were adhered to both front waist regions and back waist regions of the pants. The waist elastics were 0.8 inch (20 mm) wide and extended across the entire lateral width of the pants. One lateral side edge of each waist elastic was generally aligned with the corresponding longitudinal edge margin of the front and back waist region of the pants.
4. The absorbent structure was wrapped in tissue and both the absorbent structure and tissue were cut in the shape of an "I" and adhered to the outer cover.
5. The bodyside liner was placed over and adhered to the outer cover and absorbent.
6. Containment flaps were adhered to the liner and placed just outside of each absorbent structure lateral edge. Both flaps extended the longitudinal length of the pants.
7. The front and back lateral edges of the article were adhered together. This produced a waist and leg opening, completing the pants.

Pants 2 was a one-piece stretchable pants design made of materials commonly used in stretchable pants. Pants 2 included front and back waistbands made of the LYCRA material of Sample 1, left and right leg elastics made of the LYCRA material of Sample 1, an outer cover made of a stretchable film and nonwoven laminate material of Sample 3, a bodyside liner made of the spunbond material of Sample 5, and an absorbent structure made of a coform absorbent material of Sample 7. The absorbent structure of Pants 2 was free of weakening elements or slits of any kind.

The adhesive used to attach the outer cover and bodyside liner to the absorbent structure of Pants 2 comprised a hot melt adhesive available from Bostik-Findley Adhesive of Wauwautosa, Wis. and designated as A2525. Double-sided adhesive tape available from 3M Company of Minneapolis, Minn. and designated as No. 9509 was also used in the assembly of the pants.

Pants 2 was similar size and shape to Pants 1 and was constructed using the same technique and steps as set forth above for Pants 1.

Figure 7:
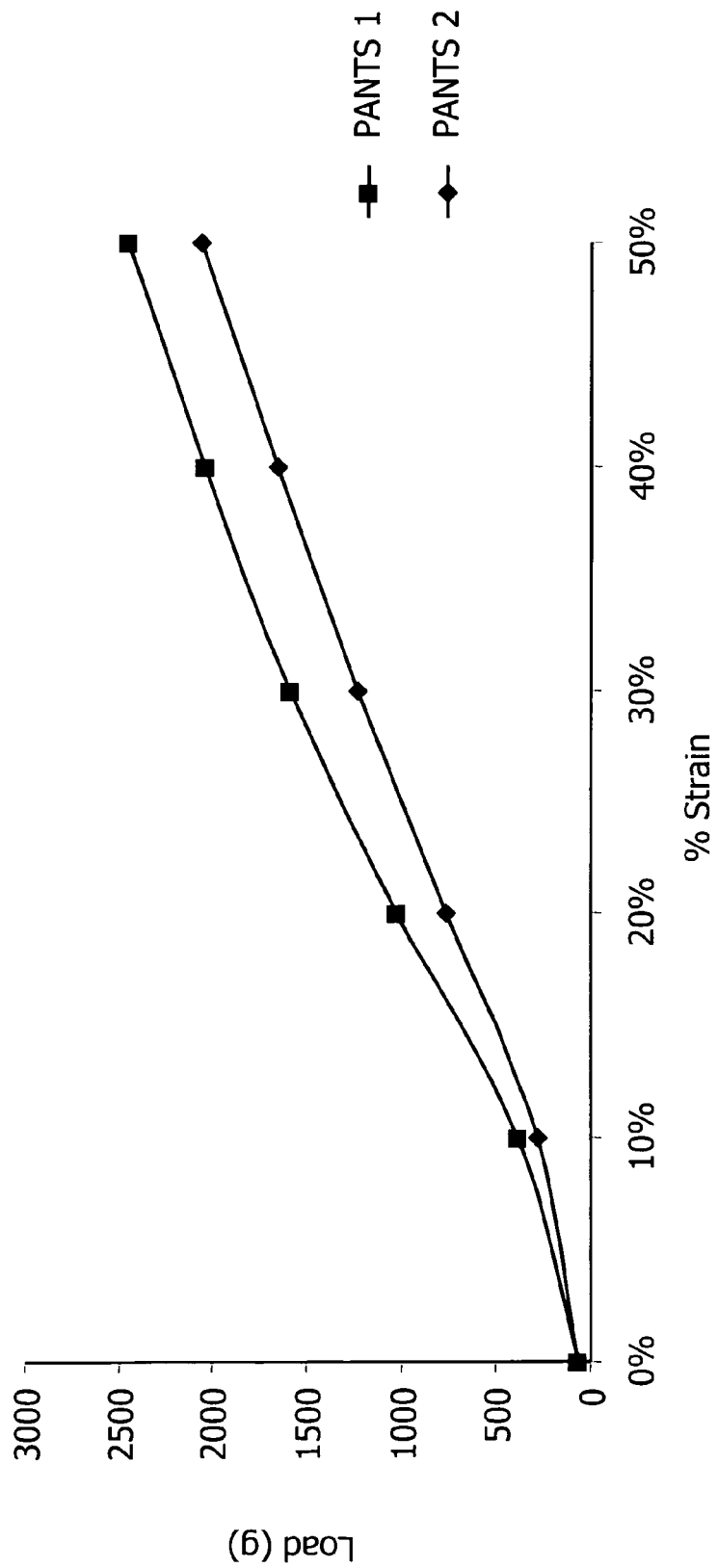
FIGS. 7-9 are plots of data obtained in a second experiment.
Figure 8:
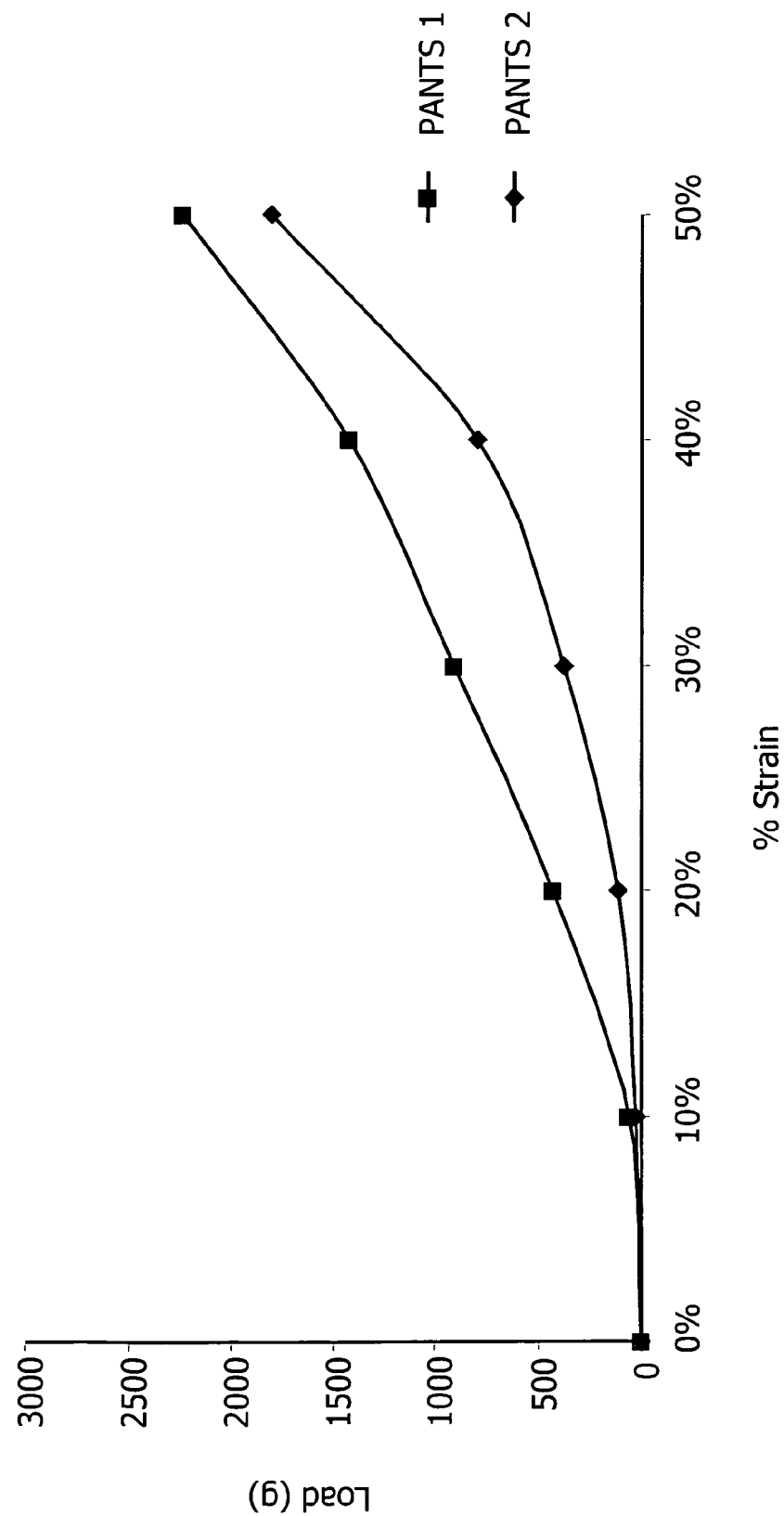
Figure 9:
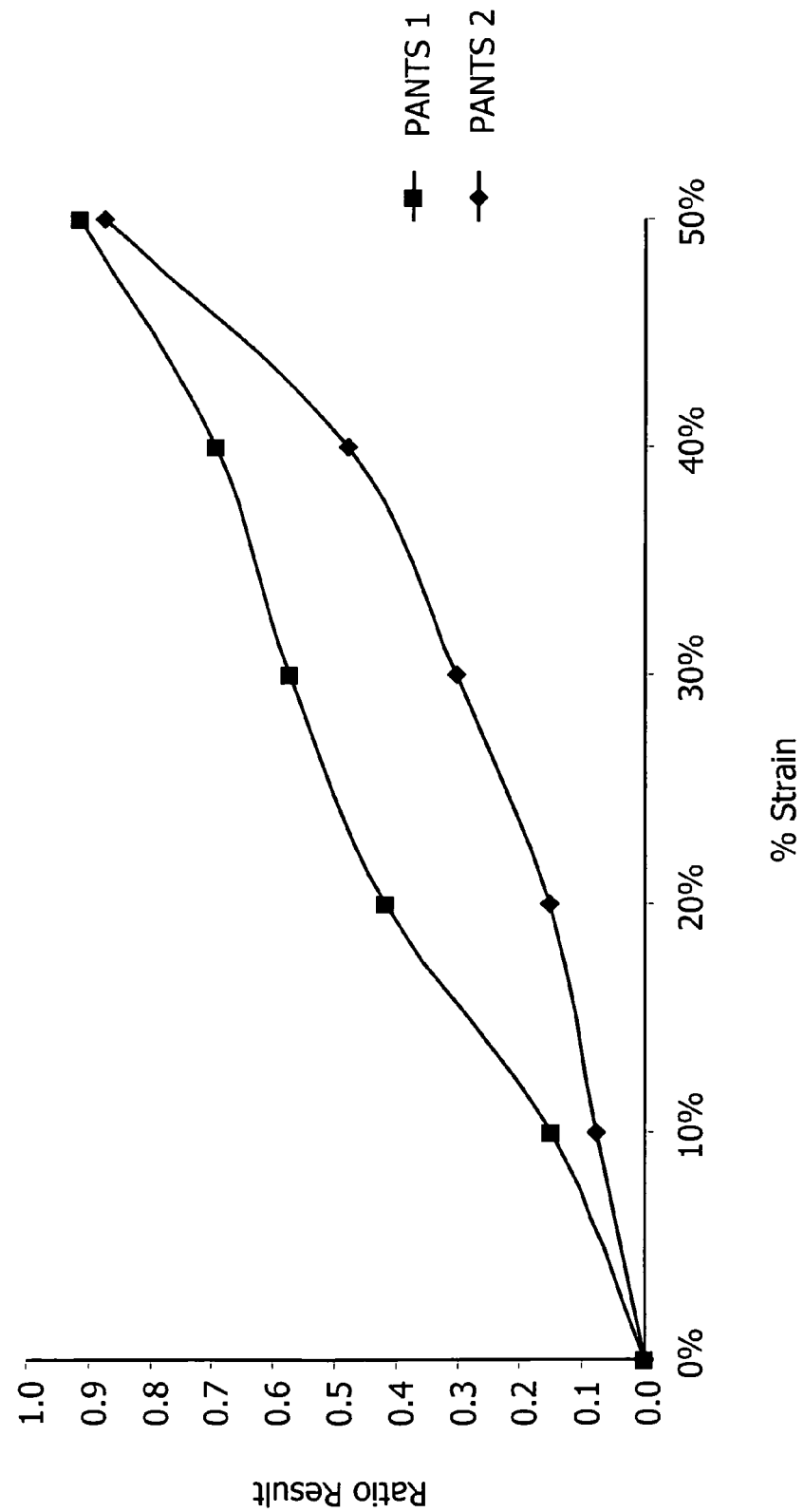

Plots comparing the test results of the second experiment are provided in FIGS. 7-9 and Tables 4-6 below. Specifically, FIG. 7 and Table 4 provide the extension loading of each of the pants at various strains; FIG. 8 and Table 5 provide the retraction loadings of the pants at various strains; and FIG. 9 and Table 6 provide the ratio of the retraction loading to the extension loading of the pants at various strains. Pants 1 having a latex rubber outer cover has a higher ratio of retraction loading to extension loading across strains ranging from 10 percent to 50 percent than Pants 2 having conventional outer cover material. As shown in FIG. 8 and Table 5, the higher ratio is a result of the increased retraction loading present in Pants 1. Thus, an absorbent article having the materials of Pants 1 provides higher retraction loadings and a higher ratio of retraction loading to extension loading, thereby resulting in an absorbent article having an improved fit.

TABLE 4

Pant Extension Loading (grams)

| | Strain 0% | Strain 10% | Strain 20% | Strain 30% | Strain 40% | Strain 50% |
|---|---|---|---|---|---|---|
| Pant 1 | 70.0 | 388.1 | 1030.3 | 1582.8 | 2042.3 | 2447.5 |
| Pant 2 | 70.0 | 280.6 | 763.1 | 1231.6 | 1652.8 | 2060.9 |

TABLE 5

Pant Retraction Loading (grams)

| | Strain 0% | Strain 10% | Strain 20% | Strain 30% | Strain 40% | Strain 50% |
|---|---|---|---|---|---|---|
| Pant 1 | 0.0 | 57.6 | 430.2 | 903.3 | 1416.1 | 2238.9 |
| Pant 2 | 0.0 | 22.1 | 117.1 | 371.1 | 787.8 | 1797.8 |

TABLE 6

Ratio of Retraction Loading to Extension Loading

| | Strain 0% | Strain 10% | Strain 20% | Strain 30% | Strain 40% | Strain 50% |
|---|---|---|---|---|---|---|
| Pant 1 | 0.00 | 0.15 | 0.42 | 0.57 | 0.69 | 0.91 |
| Pant 2 | 0.00 | 0.08 | 0.15 | 0.30 | 0.48 | 0.87 |

Material Tensile Test

For purposes of the present invention, the measurement of extension loading and retraction loading of a material or component can be determined by the following specifications and particulars.

Equipment

1. A suitable testing device is a SINTECH constant rate of extension tensile tester (available from MTS Systems Corporation, (a business having offices located in Eden Prairie, Minn.) or an equivalent device. The tensile tester is operatively programmed with suitable software (available from MTS Systems corporation), or an equivalent software.
2. Pneumatic-action grips having a 1 inch (25.4 mm) by 3 inch (76.2 mm) grip face.
3. Test facility having a temperature of 23±6 degrees Celsius, and a relative humidity of 50±10 percent.

The test samples can be cut with a precision cutter (available from Thwing-Albert Company, a business having offices located in Philadelphia, Pa.) or an equivalent device. The test sample width is perpendicular to the direction of the tensile force applied during the testing. Gage length refers to the distance between the jaws. The sample is clamped in the jaws such that no slippage occurs during elongation of the sample and the 3-to-1 gage length to width ratio of the unstretched sample is present. The moving jaw travels at a constant rate of 250 mm/min. Upon reaching a load of 10 g a 3 cycle test is initiated and the rate of movement of the moving jaw changes to 500 mm/min. The gage length at the load of 10 g is the initial gage length in which percent extension or strain calculations are derived. The moving jaw travels a distance equal to 50 percent of the original initial gage length at 10 g of loading. Upon 50 percent extension from the initial gage length, the moving jaw returns to the original 10 g load test initiation position, resulting in one complete cycle and the immediate beginning of the second cycle. A second and third cycle is completed following the same procedure of the first cycle. When the third cycle return reaches the initial gage length the 3 cycle test is completed.

The percentage of stretch extension or percent strain can be determined in accordance with the following formula;

$$100*(L-LO)/(LO)$$

where: LO=gage length at 10 g load, and

L=a distance of extension post test start.

In the material sample example described herein extension loading values at strain points 0%, 10%, 20%, 30%, 40%, 50% were collected during the first cycle extension from the position of 0% strain to the position of 50% strain. Retraction loading values at strain points 50%, 40%, 30%, 20%, 10%, and 0% were collected during the third cycle retraction from the position of 50% strain to the position of 0% strain. Three extension loading values and three retraction loading values were calculated for each strain point and a respective average extension loading and retraction loading value for each strain point was calculated. The ratio of retraction loading to extension loading can be determined in accordance to the following formula.

$$(R)/(E)$$

where: R=third cycle retraction loading at strain point A and

E=first cycle extension loading at strain point A.

In determining the extensibility or elastic nature of a material to be tested, a sample may be taken from a manufactured web or from a finished article. Also, the length of the sample should correspond to the lateral direction of the product and the width of the sample should correspond to the longitudinal direction of the sample. Further, when cutting samples from an existing product to test lateral stretch distribution, the samples should be cut from either the front waist region or the back waist region of the product.

Where a sample is prepared from a manufactured web (prior to its incorporation in a product), specimens should be obtained from a segment of the web with consistent and even formation, such as along the midline of the web. The samples should be cut from the web in the orientation as would be found in the finished product. Where the desired materials cannot be obtained from a manufactured web, the sample may be extracted from within the product. Care should be taken to avoid stretching layers during separation. The sample to be separated should be cut to the desired specimen dimensions, or, depending on adhesive chemistry, the sample section may be treated with a solvent selected to dissolve a binding adhesive without affecting the structure or properties of the constituent layers. Each specimen to be tested should be free from attachment to any other auxiliary components that may be present, such as leg, waist and/or flap elastic structures, side panels, etc., at least in the region to be tested. All specimens of a given sample should be tested at the same dimensions.

Where a given material or product will not permit specimens of the desired dimensions to be prepared, the preferred material dimensions selected should have a gage length that is at least three times the sample width. Using the aforementioned SINTECH testing device, the samples may have a width of at least approximately ¼ inch (6 mm) and a gage length of at least approximately ¾ inch (19 mm). It is contemplated that other machines may be able to test smaller samples in accordance with this testing procedure.

Absorbent Article Tensile Test

For the purposes of the present invention, the measurement of extension loading and retraction loading of an absorbent article (e.g., such as the training pants 20 can be determined by the following specifications and particulars.

Equipment

1. A suitable testing device is a SINTECH constant rate of extension tensile tester (available from MTS Systems Corporation, (a business having offices located in Eden Prairie, Minn.) or an equivalent device. The tensile tester is operatively programmed with suitable software (available from MTS Systems corporation), or an equivalent software.

2. Two Pneumatic-action grips having a 1 inch (25.4 mm) by 3 inch (76.2 mm) grip face.

3. Two cantilever fixtures having a horizontal rectangular face and a horizontal cylinder. This fixture is used as an interface between the pneumatic jaws and the pants. The rectangular face of each fixture is clamped into the 1 by 3 inch jaws such that the cylinders face one another and are opposite of one another. The cylinders have a smooth surface, are 87 mm in diameter, and are able rotate.

4. Test facility having a temperature of 23±6 degrees Celsius, and a relative humidity of 50±10 percent.

5. The gage length or circumference around the two cylinders is to be small enough such that any extension of the article to mount it on the cylinders induces less than a 70g load. The article is placed on the cylinders such that the front waist of the pants is slipped over both cylinders and each cylinder fully extends thru each leg opening. The longitudinal direction of the pants is to be perpendicular to the direction of the tensile force applied during the testing. The moving cylinder travels at a constant rate of 250 mm/min. Upon reaching a load of 70 g a 3 cycle test is initiated and the rate of movement of the moving cylinder changes to 500 mm/min. The gage length or circumference around the separating cylinders at the load of 70 g is the initial gage length in which percent extension calculations or strain calculations are derived. The moving cylinder travels a distance equal to 50 percent of the original initial gage length at 70 g of loading. Upon 50 percent extension from the initial gage length, the moving cylinder returns to the original 70 g load test initiation position, resulting in one complete cycle and the immediate beginning of the second cycle. A second and third cycle is completed following the same procedure of the first cycle. When the third cycle return reaches the initial gage length the 3 cycle test is completed.

The percentage of stretch extension or percent strain can be determined in accordance with the following formula:

$$100*(L-LO)/(LO);$$

where: LO=gage length or circumference around both cylinders at 70 g load, and

L=a measurement of the circumference around the cylinders post test start.

In the absorbent article example described herein extension loading values at strain points 0%, 10%, 20%, 30%, 40%, 50% were collected during the first cycle extension from the position of 0% strain to the position of 50% strain. Retraction loading values at strain points 50%, 40%, 30%, 20%, 10%, and 0% were collected during the third cycle retraction from the position of 50% strain to the position of 0% strain. Three extension loading values and three retraction loading values were calculated at each strain point and a respective average extension loading and retraction loading value for each strain point was calculated. The ratio of retraction loading to extension loading can be determined in accordance to the following formula:

$$(R)/(E)$$

where: R=third cycle retraction loading at strain point A and
E=first cycle extension loading at strain point A.

When introducing elements of the present invention or the preferred aspect(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or illustrated in the accompanying drawings shall be interpreted as illustrative and not in a limiting sense.

What is claimed is:

1. A stretchable absorbent article having a longitudinal axis, a lateral axis, a front waist region, a back waist region, a crotch region extending longitudinally between and interconnecting said front and back waist regions, a length, and a width, said absorbent article comprising:
    a liquid impermeable outer cover stretchable in at least one direction;
    a liner in opposed relationship with the outer cover and stretchable in at least one direction, at least one of the liner and the outer cover having a width substantially equal to the width of the absorbent article along the length thereof; and
    an absorbent structure disposed between the liner and the outer cover and extending from the crotch region to at least one of the front waist region and the back waist region of the article, said absorbent structure comprising at least one weakening element located in said at least one of the front waist region and back waist region for reducing the resistance of the absorbent structure and thereby the absorbent article to stretching, wherein the crotch region is free from weakening elements,
    the absorbent article having a retraction loading, an extension loading, and a ratio of retraction loading to extension loading as measured by an Absorbent Article Tensile Test, the ratio of retraction loading to extension loading of the absorbent article being between about 0.1 and 0.15 for a strain of approximately 10 percent as measured by said Absorbent Article Tensile Test.

2. The absorbent article set forth in claim 1 wherein the article has a ratio of retraction loading to extension loading of between about 0.20 and about 0.40 for a strain of approximately 20 percent as measured by the Absorbent Article Tensile Test.

3. The absorbent article set forth in claim 1 wherein the article has a ratio of retraction loading to extension loading of between about 0.35 and about 0.6 for a strain of approximately 30 percent as measured by the Absorbent Article Tensile Test.

4. The absorbent article set forth in claim 1 wherein the article has a ratio of retraction loading to extension loading of between about 0.53 and about 0.70 for a strain of approximately 40 percent as measured by the Absorbent Article Tensile Test.

5. The absorbent article set forth in claim 1 wherein said outer cover is elastic.

6. The absorbent article set forth in claim 5 wherein said outer cover comprises a rubber film.

7. The absorbent article set forth in claim 6 wherein said outer cover comprises a latex rubber film.

8. The absorbent article set forth in claim 5 wherein said outer cover comprises a synthetic rubber film.

9. The absorbent article set forth in claim 1 further comprising laterally opposite side portions formed integrally with the outer cover of said article.

10. A stretchable absorbent article having a longitudinal axis, a lateral axis, a front waist region, a back waist region, a crotch region extending longitudinally between and interconnecting said front and back waist regions, a length, and a width, said article comprising:
    a liquid impermeable outer cover that is elastic in at least one direction;
    a liner in opposed relationship with the outer cover and stretchable in at least one direction, at least one of the liner and the outer cover having a width substantially equal to the width of the absorbent article along the length thereof; and
    an absorbent structure disposed between the liner and the outer cover and extending from the crotch region to at least one of the front waist region and the back waist region of the article, the absorbent structure being stretchable in at least one direction, wherein the absorbent structure is stretchable in only at least one of the front waist region and the back waist region,
    the outer cover having a retraction loading, an extension loading, and a ratio of retraction loading to extension loading as measured by a Material Elongation Tensile Test, the ratio of retraction loading to extension loading being between about 0.15 and about 0.50 for a strain of approximately 10 percent.

11. The absorbent article set forth in claim 10 wherein the ratio of the outer cover retraction loading to extension loading is between about 0.35 and about 0.70 for a strain of approximately 20 percent as measured by the Material Tensile Test.

12. The absorbent article set forth in claim 10 wherein the ratio of the outer cover retraction loading to extension loading is between about 0.45 and about 0.70 for a strain of approximately 30 percent as measured by the Material Tensile Test.

13. The absorbent article set forth in claim 10 wherein the ratio of the outer cover retraction loading to extension loading is between about 0.60 and about 0.80 for a strain of at least approximately 40 percent as measured by the Material Tensile Test.

14. The absorbent article set forth in claim 10 wherein the ratio of the outer cover retraction loading to extension loading is between about 0.85 and about 0.90 for a strain of approximately 50 percent as measured by the Material Tensile Test.

15. The absorbent article set forth in claim 10 wherein the outer cover comprises at least one rubber film.

16. The absorbent article set forth in claim 15 wherein the outer cover comprises at least one latex rubber film.

17. The absorbent article set forth in claim 15 wherein said outer cover comprises at least one synthetic rubber film.

18. The absorbent article set forth in claim 10 wherein said absorbent structure comprises at least one weakening element.

19. The absorbent article set forth in claim 10 further comprising laterally opposite side portions formed integrally with the outer cover of the article.

* * * * *